(12) United States Patent
Ebinuma et al.

(10) Patent No.: US 6,969,613 B1
(45) Date of Patent: Nov. 29, 2005

(54) METHOD FOR DETERMINATION OF HYDROGEN SULFIDE OR SULFIDE ION AND METHOD FOR DETERMINATION OF SPECIFIC SUBSTANCE UTILIZING SAID METHOD

(75) Inventors: Hiroyuki Ebinuma, Ryugasaki (JP); Koji Ushizawa, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/856,790

(22) PCT Filed: Dec. 7, 1999

(86) PCT No.: PCT/JP99/06847

§ 371 (c)(1),
(2), (4) Date: May 25, 2001

(87) PCT Pub. No.: WO00/34771

PCT Pub. Date: Jun. 15, 2000

(30) Foreign Application Priority Data

| Dec. 7, 1998 | (JP) | ................................. 10-347003 |
| Mar. 26, 1999 | (JP) | ................................. 11-084035 |
| May 27, 1999 | (JP) | ................................. 11-147848 |

(51) Int. Cl.[7] ............................................ G01N 33/00
(52) U.S. Cl. ...................... 436/120; 436/119; 436/164; 435/4; 435/232; 435/130
(58) Field of Search ........................ 436/120, 119, 164; 435/4, 232, 130

(56) References Cited

U.S. PATENT DOCUMENTS 5,985,540 A * 11/1999 Tan et al. ........................ 435/4

6,107,100 A * 8/2000 Dabovic ........................ 436/119

FOREIGN PATENT DOCUMENTS

| EP | 0 584 568 A | 3/1994 |
| GB | 2 200 989 A | 8/1988 |

(Continued)

OTHER PUBLICATIONS

P. Sharma et al, "Studies on Metal-Metal Sulphide Electrodes: Part I—Application of Arsenic-Arsenic Sulphide, Antimony-Antimony Sulphide & Molybdenum-Molybdenum Sulphide Electrodes in the Quantitative Determination of Sulphide Ion", *Indian Journal of Chemistry*, vol. 21A, pp. 259-263 (Mar. 1982).

(Continued)

*Primary Examiner*—Monique T. Cole
(74) *Attorney, Agent, or Firm*—Frishauf, Holtz, Goodman & Chick, P.C.

(57) ABSTRACT

The present invention provides a method for quantitatively determining hydrogen sulfide or sulfide ions conveniently with high sensitivity, which comprises adding to a sample containing hydrogen sulfide or sulfide ions, metal ions or a compound which liberates said metal ions and a metal indicator which reacts with the metal ions and resultingly undergoes color development, wherein the color development is accelerated or inhibited by the hydrogen sulfide or sulfide ions; and measuring the degree of color development of the metal indicator. The present invention further provides a method for quantitatively determining a specific substance, which comprises adding to a sample containing a specific substance, a component which acts on the specific substance so that the specific substance forms hydrogen sulfide or sulfide ions, metal ions or a compound which liberates said metal ions, and a metal indicator which reacts with the metal ions and resultingly undergoes color development, wherein the color development is accelerated or inhibited by the hydrogen sulfide or sulfide ions; and measuring the degree of color development of the metal indicator.

20 Claims, 2 Drawing Sheets

FOREIGN PATENT DOCUMENTS

| | | |
|---|---|---|
| JP | 54-99494 A | 8/1979 |
| JP | 63-247656 A | 10/1988 |
| JP | 6-160368 A | 6/1994 |

OTHER PUBLICATIONS

A. Svenson, "Rapid and Sensitive Spectrophotometric Method for Determination of Hydrogen Sulfide with 2, 2'-Dipyridyl Disulfide", *Anal. Biochem.*, vol. 107, pp. 51-55 (1980).

M.F. Mousavi et al, "Spectrophotometric Determination of Trace Amounts of Sulfide Ion Based on Its Catalytic Reduction of Toluidine Blue", *The Chem. Soc. of Japan*, vol. 65, No. 10, pp. 2770-2772 (1992).

I.G. Gökman et al, "Determination of Selenium in Biological Matrices Using a Kinetic Catalytic Method", *Analyst*, vol. 119, pp. 703-708 (1994).

* cited by examiner

METHOD FOR DETERMINATION OF HYDROGEN SULFIDE OR SULFIDE ION AND METHOD FOR DETERMINATION OF SPECIFIC SUBSTANCE UTILIZING SAID METHOD

This application is a national phase application of International Application No. PCT/JP99/06847 (not published in English) filed Dec. 7, 1999.

Method for quantitatively determining hydrogen sulfide or sulfide ions, and method for quantitatively determining a specific substance utilizing it

TECHNICAL FIELD

The present invention relates to a method for quantitatively determining hydrogen sulfide or sulfide ions in a sample conveniently with high sensitivity, by utilizing an acceleration or inhibition reaction by hydrogen sulfide or sulfide ions against formation of complexes between metal ions and a metal indicator; and a method for quantitatively determining a specific substance in a sample conveniently with high sensitivity, wherein hydrogen sulfide is formed from the specific substance and the hydrogen sulfide or sulfide ions derived therefrom are measured by utilizing the above quantitative determination method.

BACKGROUND ART

Sulfur is one of elements which take important roles in nature. Particularly, it takes a substantial role as a constituting element for cysteine and methionine as sulfur-containing amino acids. Further, it has been known that a large sulfur cycle is carried out between plants and animals. In the plants, sulfur is taken in the form of sulfate ions and reduced to sulfide ions, and then subjected to cysteine synthesis and further methionine synthesis. In the animals, methionine is ingested from foods by food chain and metabolized to cysteine in vivo. In this metabolization stage, homocysteine is formed as an intermediate.

Homocysteine is an intermediary metabolite which is scarcely present at the normal condition. However, it has been reported that when its concentration in blood is at a high level, the rate of occurrence of coronary disease and cerebral apoplexy is high. Accordingly, the homocysteine amount in blood is already recognized or still unrecognized to be a risk factor useful for predicting the occurrence of thromboembolism such as myocardial infarction or cerebral infarction, or arteriosclerosis.

Further, since cysteine is an amino acid formed by metabolism of methionine, it may be an auxiliary index for grasping the causes of metabolic error of homocysteine.

Furthermore, enzymes are known which have a function of acting on homocysteine or cysteine and conducting decomposition or substitution, thereby forming hydrogen sulfide. However, even if it is attempted to quantitatively determine homocysteine or cysteine by utilizing such enzymes, since there is no method for measuring the formed hydrogen sulfide conveniently with high sensitivity, no practical method has been found in which these enzymes are used for quantitatively determining homocysteine or cysteine.

On the other hand, hydrogen sulfide or sulfide ions derived therefrom are important as an index of environmental pollution such as air pollution or water pollution of rivers. The state of pollution can be confirmed by measuring the hydrogen sulfide or sulfide ions derived therefrom in samples.

As conventional methods for measuring hydrogen sulfide or sulfide ions derived therefrom, the following methods are known. For example, as a method of utilizing a color developer, a method wherein 2,2'-dipyridyldisulfide (Svenson, Anal. Biochem., 107; 51–55(1980)) or sodium nitroprusside is used, a method wherein N,N-dimethyl-P-phenylenediamine and ferric chloride are reacted in a strong acidic condition to form methylene blue and blue color development is detected (methylene blue method), a method wherein fading amount and rate of a dye (toluidine blue or methylene blue) is measured by using cerenium as a catalyst (Mousavi et al, Bull. Chem. Soc. Jpn, 65;2770–2772(1992), Gokmen et al, Analyst, 119;703–708 (1994)), and the like are known. However, these methods are hardly adequate from the viewpoints of convenience and sensitivity.

DISCLOSURE OF INVENTION

Accordingly, it is an object of the present invention to provide a more convenient and highly sensitive method for quantitatively determining hydrogen sulfide or sulfide ions. It is another object of the present invention to provide a method for quantitatively determining a specific substance in a sample conveniently with high sensitivity, wherein hydrogen sulfide is formed from the specific substance and the hydrogen sulfide or sulfide ions derived therefrom are measured by utilizing the above quantitative determination method.

The present inventors have conducted intensive studies to accomplish the above objects, and found that hydrogen sulfide or sulfide ions in a sample can be quantitatively determined conveniently with high sensitivity by utilizing an inhibition or acceleration action by the hydrogen sulfide or sulfide ions against color development between metal ions and a metal indicator.

Namely, the present invention provides a method for quantitatively determining hydrogen sulfide or sulfide ions, which comprises adding to a sample containing hydrogen sulfide or sulfide ions, metal ions or a compound which liberates said metal ions and a metal indicator which reacts with the metal ions and resultingly undergoes color development, wherein the color development is accelerated or inhibited by the hydrogen sulfide or sulfide ions; and measuring the degree of color development of the metal indicator.

The present invention further provides a method for quantitatively determining a specific substance, which comprises adding to a sample containing the specific substance, a component which acts on the specific substance so that the specific substance forms hydrogen sulfide or sulfide ions, metal ions or a compound which liberates said metal ions, and a metal indicator which reacts with the metal ions and resultingly undergoes color development, wherein the color development is accelerated or inhibited by the hydrogen sulfide or sulfide ions; and measuring the degree of color development of the metal indicator.

According to the present invention, it is possible to quantitatively determine hydrogen sulfide or sulfide ions conveniently with high sensitivity, by utilizing an acceleration or inhibition reaction by the sulfide ions against formation of complexes between metal ions and a metal indicator. It is further possible to quantitatively determine a specific substance in a sample conveniently with high sensitivity, by adding a component which acts on the specific substance so that the specific substance forms hydrogen sulfide or sulfide ions to the sample, and measuring the formed hydrogen sulfide utilizing the above reaction.

BEST MODE FOR CARRYING OUT THE INVENTION

Figure 1:
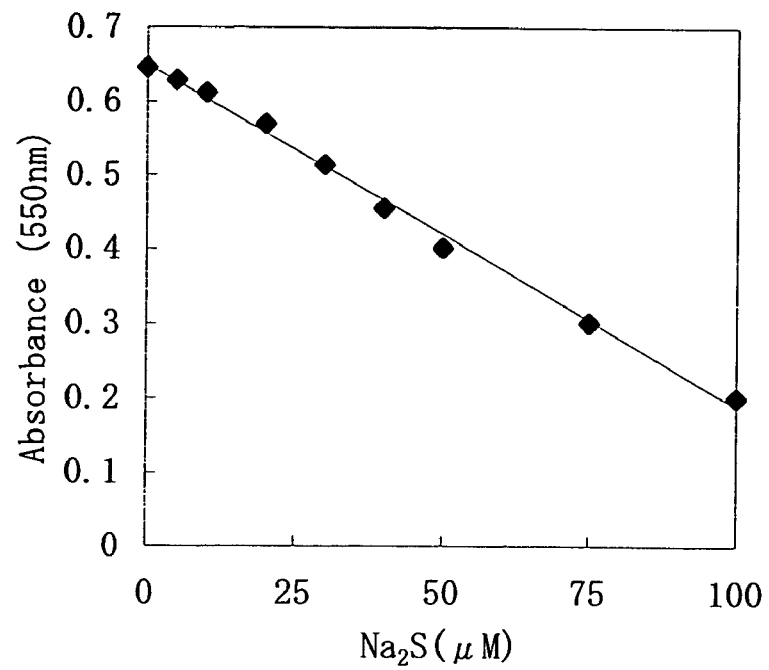
FIG. 1 is a graph showing the results of quantitative determination of sulfide ions by a color development-inhibiting method.

In the method for quantitatively determining hydrogen sulfide or sulfide ions of the present invention, the case of utilizing the action of hydrogen sulfide or sulfide ions which inhibit the color development reaction between metal ions and a metal indicator, will be described hereinbelow. That is, the hydrogen sulfide or sulfide ions present in a sample are allowed to contact with metal ions to form a metal sulfide, and at the same time, the metal ions are reacted with the metal indicator, and then the degree of color development is measured, whereby the amount of the complexes formed by the reaction between the metal ions and the metal indicator is determined. Then, the above amount of the formed complexes is subtracted from the amount of the formed complexes when the metal ions are reacted with the metal indicator under the same conditions as in the above, provided that no hydrogen sulfide or sulfide ions are present, whereby the decreased amount of the formed complexes is obtained by utilizing the characteristic that the metal sulfide forms no complexes. The decreased amount of the formed complexes corresponds to the amount of the hydrogen sulfide or sulfide ions present in the sample. Accordingly, the amount of the hydrogen sulfide or sulfide ions in the sample can be calculated based on the decreased amount of the formed complexes.

The case of utilizing the action of hydrogen sulfide or sulfide ions which accelerates the color development reaction between the metal ions and the metal indicator, will be described hereinbelow. That is, into the sample containing the hydrogen sulfide or sulfide ions, the metal ions and the metal indicator are added, and a reaction is carried out, and then the degree of color development is measured to determine the amount of the complexes formed by the reaction between the metal ions and the metal indicator. Then, from this amount of the formed complexes, the amount of the complexes formed when the metal ions are reacted with the metal indicator under the same conditions as in the above, provided that no hydrogen sulfide or sulfide ions are present, is subtracted, whereby the increased amount of the formed complexes is determined. Since the increased amount of the formed complexes is attributable to the acceleration of the reaction between the metal ions and the metal indicator by the hydrogen sulfide or sulfide ions, it corresponds to the amount of the hydrogen sulfide or sulfide ions. Accordingly, the amount of the hydrogen sulfide or sulfide ions in the sample can be calculated based on the increased amount of the formed complexes.

In the present invention, the metal ions are not particularly limited so long as the color development between the metal ions and the metal indicator is inhibited or accelerated by the hydrogen sulfide or sulfide ions. As the one inhibiting the color development reaction of the metal ions and the metal indicator, zinc ions are preferably used. As the one accelerating the above color development reaction, iron (II) and (III) ions are preferably used. Specifically, hydrochlorides, sulfates, acetates or the like of the above metals are used. However, there is no particular limitation so long as it dissolves in an aqueous solution and forms liberated metal ions.

As the metal indicator used in the present invention, there is no particular limitation so long as it is a substance of which the color development reaction with the metal ions is inhibited or accelerated by the hydrogen sulfide or sulfide ions. Preferred is the one having a high sensitivity of color development at the time of forming the complexes. For example, pyridylazo compounds and nitrosoaminophenol compounds are preferably used. Further specifically, as the pyridylazo compounds, 2-(5-bromo-2-pyridylazo)-5-[N-n-propyl-N-(3-sulfopropyl)amino]phenol sodium salt (trade name: 5BrPAPS; hereinafter simply referred to as 5Br.PAPS) and 2-(5-nitro-2-pyridylazo)-5-[N-n-propyl-N-(3-sulfopropyl)-amino]phenol sodium salt (trade name: Nitro.PAPS) are preferably used. Further, as the nitrosoaminophenol compounds, 2-nitroso-5-[N-N-propyl-N-(3-sulfopropyl)-amino]phenol (trade name: Nitroso.PSAP) and 2-nitroso-5-[N-ethyl-N-(3-sulfopropyl)amino]phenol (trade name: Nitroso.ESAP) are preferably used. These compounds are water soluble and have a property that they form complexes with zinc ions, copper ions, cobalt ions or iron ions and undergo color development with a high sensitivity. As these metal indicators, ones having various characteristics are commercially sold and available from, for example, DOJINDO LABORATORIES.

The specific substance in the present invention may be any substance so long as it forms hydrogen sulfide or sulfide ions by e.g. enzymatic reaction. For example, homocysteine and cysteine are preferably mentioned.

When the specific substance is homocysteine, as the component for forming hydrogen sulfide or sulfide ions from the specific substance, an enzyme (E1) which has a function of acting on homocysteine so that the homocysteine would form hydrogen sulfide or sulfide ions, is used. As such an enzyme, for example, L-methionine-γ-lyase (enzyme No. EC class 4.4.1.11) and O-acetylhomoserine-lyase (enzyme No. EC class 4.2.99) may be mentioned. Particularly, O-acetylhomoserine-lyase may preferably be used. forming hydrogen sulfide.

L-methionine-γ-lyase is known as an enzyme that shows a decomposition (liberation) action against homocysteine and forms hydrogen sulfide in the absence of a thiol compound, but shows an action of catalyzing γ-substitution in the presence of a thiol compound. This enzyme is obtainable from microorganisms which are capable of producing it, for example, bacteria of the Pseudomonas genus, but some types thereof are commercially sold and available from, for example, Wako Pure Chemical Industries, Ltd..

Further, O-acetylhomoserine-lyase is known as an enzyme that has an amino acid-synthesizing action (for example, an action of forming homocysteine from O-acetylhomoserine and hydrogen sulfide, and methionine from methanethiol) see the "Handbook of Enzyme", compiled by Maruo et al, Asakura Shoten, 1982). The present inventors have newly found an enzymatic action that when O-acetylhomoserine-lyase is allowed to act on homocysteine in the presence of a thiol compound, hydrogen sulfide is formed by γ-substitution (Japanese Patent Application No. 10-347003).

With respect to O-acetylhomoserine-lyase, various microorganisms that are capable of producing it have been known see, for example, Ozaki et al, J. Biochem 91; 1163–1171 (1982), Yamagata, J. Biochem 96; 1511–1523(1984), Brzywczy et al, Acta. Biochimica. Polonica 40(3); 421–428 (1993)). O-Acetylhomoserine-lyase may be obtained by culturing these microorganisms, but some types thereof are commercially sold and available from, for example, Yunitica Ltd. These enzymes (E1) have a function of strongly acting on homocysteine and acting a little on cysteine, thereby forming hydrogen sulfide.

Physicochemical properties of O-acetylhomoserine-lyase (trade name:"GCS") derived from Bacillus genus, manufactured by Yunitica Kabushiki Kaisha, are as follows. Among the following physicochemical properties, items other than molecular weight were determined by the present inventors.

Physicochemical Properties

1) Action: it catalyzes γ-substitution of L-homocysteine and a thiol compound, thereby forming hydrogen sulfide and a thiol compound-substituted homocysteine. Further, it catalyzes a substitution of L-methionine and a thiol compound, thereby forming methane thiol and a thiol compound-substituted homocysteine.

2) Substrate specificity: it acts on L-homocysteine and L-methionine. Further, it acts a little on L-cysteine by β-substitution.

3) Molecular weight: 180,000 (gel filtration method)
4) Optimum pH: 8.5–9.0
5) Km: 0.9 mM (L-homocysteine)

Further, when the specific substance is cysteine, as the component for forming hydrogen sulfide or sulfide ions from the specific substance, an enzyme (E2) which has a function of acting on cysteine so that the cysteine forms hydrogen sulfide or sulfide ions, is used. As such an enzyme, for example, O-acetylserine-lyase, β-cyanoalanine synthase and cysteine lyase may be mentioned. Particularly, O-acetylserine-lyase is preferably used.

O-Acetylserine-lyase is known as an enzyme that has a cysteine-synthesizing action (an action of forming cysteine from O-acetylserine and hydrogen sulfide). The present inventors have found an enzymatic action that when O-acetylserine-lyase is allowed to act on cysteine in the presence of a thiol compound, hydrogen sulfide is formed by β-substitution (Japanese Patent Application No. 11-84035). This action is specific to cysteine. O-Acetylserine-lyase may be obtained from microorganisms that are capable of producing it (for example, Burnell et al, Biochim. Biophys. Acta 481; 246–265 (1977), Nagasaw et al, Methods Enzymol 143; 474–478(1987), plants (for example, Droux et al, Arch.. Biochem. Biophys. 295(2); 379–390(1992), Yamaguchi et al, Biochim. Biophys. Acta 1251; 91–98(1995)), etc.

For example, the following are physicochemical properties of O-acetylserine-lyase obtained from spinach by the method described in Yamaguchi et al, Biochim. Biophys. Acta 1251; 91–98(1995). Among the following physicochemical properties, items other than molecular weight were determined by the present inventors.

Physicochemical Properties of O-acetylserine-lyase

1) Action: it catalyzes β-substitution of L-cysteine and a thiol compound, thereby forming hydrogen sulfide and a thiol compound-substituted cysteine.

2) Substrate specificity: it specifically acts on L-cysteine.
3) Molecular weight: 63,000 (gel filtration method)
4) Optimum pH: 9.0–11.0
5) Km: 0.27 mM (L-cysteine)

On the other hand, it has been known that when β-cyanoalanine synthase is allowed to act on cysteine in the presence of cyan, it shows a catalytic reaction of forming hydrogen sulfide by β-substitution, and when cysteine lyase is allowed to act on cysteine in the presence of sulfite ions, it shows a catalytic reaction of forming hydrogen sulfide by β-substitution.

As the thiol compound used in the present invention, there is no particular limitation so long as it can be used for a substitution reaction, and methane thiol, 2-mercaptoethanol, dithiothreitol, thioglycerol and cysteamine may, for example, be mentioned. As the preferred ones, 2-mercaptoethanol and cysteamine may be mentioned.

The reaction in the method for measuring the hydrogen sulfide or sulfide ions of the present invention, is represented by the following Chemical Formulae 1 and 2.

Chemical Formula 1

Reaction A:
 Metal ions+Metal indicator→Formation of complexes
 (zinc) (pyridylazo compound) (color development)

Reaction B:
 Metal ions+Sulfide ions (zinc) (hydrogen sulfide)
 →Metal sulfide+Metal indicator−(inhibition)
 (zinc sulfide) (pyridylazo compound)
 →Formation of complexes (x)

Chemical Formula 2

Reaction C:
 Metal ions+Metal indicator
 (iron) (pyridylazo compound or
  nitrosoaminophenol compound)
 −(no reaction)→Formation of complexes (x)

Reaction D:
 Metal ions+Sulfide ions+Metal indicator (iron) (hydrogen sulfide) (pyridylazo compound or
  nitrosoaminophenol compound)
 −(acceleration of reaction)→Formation of complexes
  (color development)

In the above Chemical Formula 1, Reaction A shows that in the absence of sulfide ions, the metal ions (for example, zinc ions) and the metal indicator (for example, a pyridylazo compound) form complexes rapidly and undergo color development.

Reaction B shows that by preliminarily allowing the metal ions (for example, zinc ions) to contact with sulfide ions to form a metal sulfide (for example, zinc sulfide), the formed compound (zinc sulfide) can not form complexes with the metal indicator, and the numerical value of color development decreases correspondingly. Accordingly, by calculating the decreased amount of the numerical value of color development, hydrogen sulfide or sulfide ions can be measured.

Namely, in the above Chemical Formula 1, it is important to select the combination of metal ions which form a stable metal sulfide by reacting with sulfide ions, and a metal indicator which forms complexes rapidly with the metal ions. As such a combination of the metal ions and the metal indicator, for example, the combination of zinc ions and a pyridylazo compound may be mentioned. In the explanation hereinbelow, the measurement method utilizing the principle of the above Chemical Formula 1 is called a color development-inhibiting method.

Further, in the above Chemical Formula 2, Reaction C shows that, for example, by preliminarily allowing metal ions (e.g. iron ions) and a metal indicator (e.g. a pyridylazo compound or a nitrosoaminophenol compound) to co-present in a suitable buffer solution of from neutral to week alkaline condition (pH 7.0–9.0), the formation of complexes between the metal ions and metal indicator is inhibited and therefore no color development occurs.

Reaction D shows that in such a condition, when sulfide ions are added thereto, the formation of complexes thereof is accelerated corresponding to the concentration of sulfide ions, whereby the numerical value of color development is correspondingly increased. Accordingly, by calculating the increased amount of the numerical value of color development, the hydrogen sulfide or sulfide ions can be measured.

Namely, in the above Chemical Formula 2, it is important to control the conditions so that the metal ions and metal indicator hardly form complexes. As the combination of the metal ions and metal indicator, a combination of, for example, iron ions and a pyridyl compound or a nitrosoaminophenol compound, may be mentioned. In the explanation hereinbelow, the measurement method utilizing the principle of the above Chemical Formula 2 is called a color development-accelerating method.

The reaction mechanism of the above color development-accelerating method may be considered as follows with respect to the combination of the iron ions and pyridylazo compound.

It is known that iron ions are present in various forms such as an aqua complex or a hydroxso complex in an aqueous solution and substantially affected by factors such as pH conditions. Further, under a high alkaline condition, formation of precipitates as hydroxides may occur. The following may be considered. In the combination of iron ions and a pyridylazo compound in this measurement system, by preliminarily allowing iron (II) and iron (III) ions to co-present in a suitable buffer solution of from neutral to a week alkaline condition (pH 7.0–9.0), the iron ions themselves form complexes in the solution, thereby inhibiting the reaction with the metal indicator (pyridylazo compound). Particularly, in the case of iron (II) ions, under the above condition, iron (II) ions are susceptible to oxidation by oxygen in addition to the formation of complexes, whereby the iron ions are present in the form of iron (III) ions. If sulfide ions are added to the iron ions in such condition and allowed to co-present together, iron (III) ions are reduced to iron (II) ions by the reducing power of the sulfide ions, and become to be reactive with the pyridylazo compound, thereby undergoing color development. Further, some type of metal indicator hardly forms complexes with iron (III) ions, and in such a case, this principle of the acceleration method may be applied even if the pH is outside of the above-mentioned pH range.

Namely, according to the color development-accelerating method of the present invention, firstly, metal ions which become reactive with a metal indicator by the reduction with sulfide ions, are brought into a condition such that they are not reactive with the metal indicator by, for example, adjusting the conditions of the solution of metal ions appropriately. Then, by adding sulfide ions thereto, the metal ions in the non-reactive condition is changed to be reactive, and allowed to react with the metal indicator.

Accordingly, the color development-accelerating method of the present invention is accomplished by combining the above-mentioned metal ions with a suitable metal indicator.

Further, the reaction in the measurement method when the specific substance of the present invention is homocysteine and cysteine, is represented by the following Chemical Formula 3:

Chemical formula 3

Reaction E:
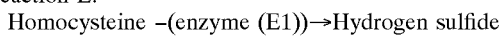

Reaction F:
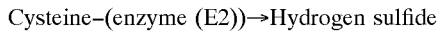

In the above Chemical Formula 3, Reaction E shows that hydrogen sulfide is formed by the action by an enzyme (E1) (for example, O-acetylhomoserine-lyase) which has a catalytic function of acting on homocysteine so that the homocysteine forms hydrogen sulfide. Further, Reaction F shows that hydrogen sulfide is formed by the action by an enzyme (E2) (for example, O-acetylserine-lyase) which has a catalytic function of acting on cysteine so that the cysteine forms hydrogen sulfide. Then, the formed hydrogen sulfide is measured by utilizing the reaction as shown in Chemical Formula 1 or 2 to quantitatively determine the homocysteine or cysteine.

Hereinbelow, the present invention will be described in further detail with reference to examples. However, it should be mentioned that the present invention is by no means restricted thereto.

Example 1 (Quantitative determination of sulfide ions by color development-inhibiting method)

As the sample and reagents, the following were used.
Sample: an aqueous solution containing from 0 to 100 $\mu$M of sodium sulfide (manufactured by Wako Pure Chemicals Industries, Ltd.) as sulfide ions.
1st reagent:
Tris buffer (pH 8.5) 100 mM
Zinc chloride 10 $\mu$M
2nd reagent:
5.BrPAPS (manufactured by DOJINDO LABORATORIES) 1 mM To 50 $\mu$l of the sample, 900 $\mu$l of the 1st reagent was added, and this was left to stand at room temperature for 5 minutes, and then 50 $\mu$l of the 2nd reagent was added thereto, and this was left to stand at room temperature for 5 minutes. Then, the absorbance of the reaction solution was measured with a wavelength of 550 nm. The results are shown in FIG. 1.

From the results of FIG. 1, decrease in the absorbance was confirmed corresponding to the concentration of the sulfide ions, and it was found that this correlation was quantitative. From the results, it was also found that sulfide ions can be measured by utilizing the inhibition reaction against the formation of complexes between the metal ions and metal indicator.

Example 2 (Quantitative determination of sulfide ions by color development-accelerating method)

As the sample and reagents, the following were used.
Sample: an aqueous solution containing from 0 to 100 $\mu$M of sodium sulfide (manufactured by Wako Junyaku K.K.) as sulfide ions.
1st reagent:
Tris buffer (pH 8.0) 100 mM
Ferrous chloride 33.3 $\mu$M
2-Mercaptoethanol 4 mM
2nd reagent:
5Br.PAPS (manufactured by Dojin Kagaku Kenkyusho K.K.) 0.25 mM
3rd reagent:
EDTA (pH 7.0) 200 mM To 20 $\mu$l of the sample, 600 $\mu$l of the 1st reagent was added, and this was left to stand at 37° C. for 10 minutes, and then 160 $\mu$l of the 2nd reagent was added thereto, and this was left to stand at 37° C. for 5 minutes. Further, 20 $\mu$l of the 3rd reagent was added thereto, and this was left to stand at room temperature for 5 minutes, and then the absorbance of the reaction solution was measured with a wavelength of 550 nm. The results are shown in FIG. 2.

Figure 2:
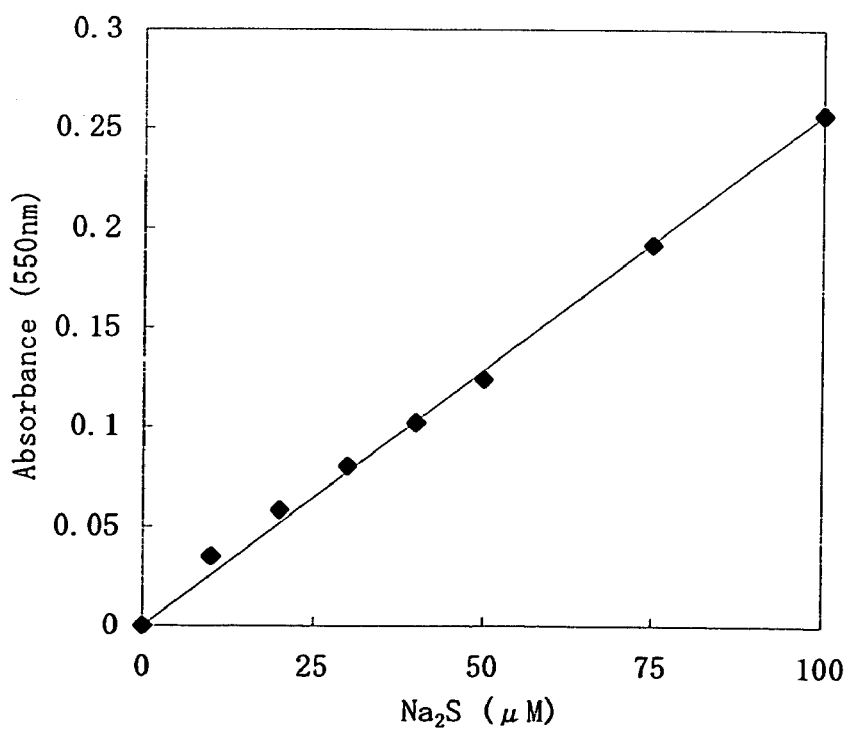
FIG. 2 is a graph showing the results of quantitative determination of sulfide ions by a color development-accelerating method.

From the results of FIG. 2, increase in the absorbance was confirmed corresponding to the concentration of the sulfide ions, and it was found that this correlation was quantitative.

From the results, it was also found that sulfide ions can be measured by utilizing the acceleration reaction for the formation of complexes between the metal ions and metal indicator.

In the following examples, as an enzyme (E1) to be used for the quantitative determination of homocysteine, O-acetylhomoserine-lyase derived from Bacillus genus (trade name:"GCS", manufactured by Yunitica Ltd., the strength indicated below is a nominal value of the manufacturer) was used, and as an enzyme (E2) to be used for the quantitative determination of cysteine, O-acetylserine-lyase (derived from spinach) was used.

The O-acetylserine-lyase was prepared in accordance with the method of Yamaguchi et al (Biochim. Biophys. Acta 1251; 91–98 (1995)).

Specifically, through the extraction from 2 kg of spinach leaves and steps of ion exchange chromatography, hydrophobic chromatography and gel filtration chromatography, the enzyme of about 4,000 units was prepared and used for the examples. The strength was measured by the method described in the above document.

Example 3 (Quantitative determination of homocysteine by color development-accelerating method)

As the sample and reagents, the following were used.

Sample: an aqueous solution containing from 0 to 50 $\mu$M of L-homocystine (manufactured by Sigma K.K.) (as the L-homocysteine, from 0 to 100 $\mu$M)

1st reagent:
Tris buffer (pH 8.0) 100 $\mu$M
Ferrous chloride 33.3 $\mu$M
2-Mercaptoethanol 4 mM
O-Acetylhomoserine-lyase (manufactured by Yunitica Ltd. 3u/ml
2nd reagent:
5Br.PAPS (manufacturedbyDojinKagakuKenkyushoK.K.) 0.25 mM
3rd reagent:
EDTA (pH 7.0) 200 mM To 20 $\mu$l of the sample, 600 $\mu$l of the 1st reagent was added, and this was left to stand at 37° C. for 10 minutes, and then 160 $\mu$l of the 2nd reagent was added thereto, and this was left to stand at 37° C. for 5 minutes. Further, 20 $\mu$l of the 3rd reagent was added thereto, and this was left to stand at room temperature for 5 minutes, and then the absorbance of the reaction solution was measured with a wavelength of 550 nm. The results are shown in FIG. 3.

Figure 3:
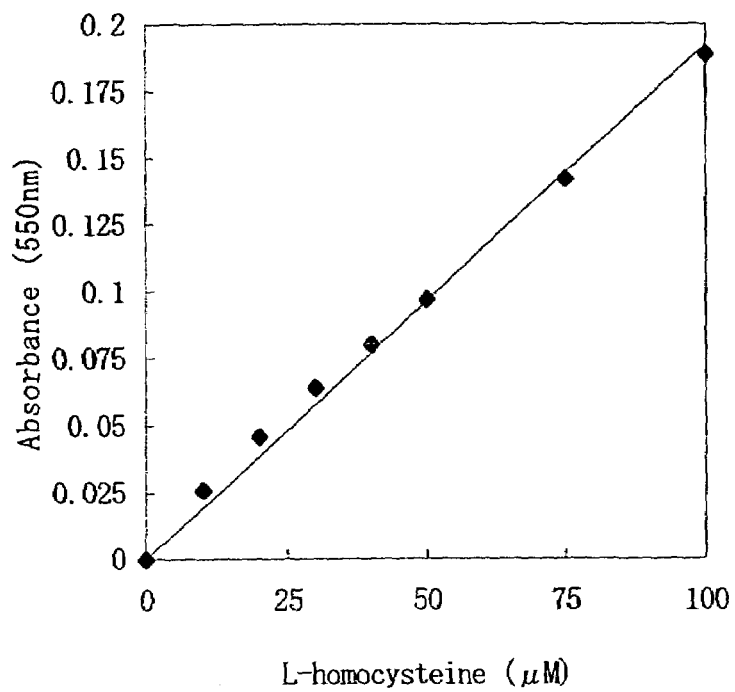
FIG. 3 is a graph showing the results of quantitative determination of homocysteine by a color development-accelerating method.

From the results of FIG. 3, increase in the absorbance was confirmed corresponding to the concentration of the homocysteine, and it was found that this correlation was quantitative. From the results, it was also found that homocysteine can be measured by utilizing the acceleration reaction for the formation of complexes between the metal ions and metal indicator.

Example 4 (Quantitative determination of cysteine by color development-accelerating method)

As the sample and reagents, the following were used.

Sample: an aqueous solution containing from 0 to 500 $\mu$M of L-cysteine (manufactured by Sigma K.K.).

1st reagent:
Tris buffer (pH 8.0) 100 mM
Ferrous chloride 33.3 $\mu$M
2-Mercaptoethanol 4 mM
O-Acetylserine-lyase (derived from spinach) 6 u/ml
2nd reagent:
5BrPAPS (manufactured by Doj in Kagaku Kenkyusho K.K.) 0.25 mM
3rd reagent:
EDTA (pH 7.0) 200 mM To 20 $\mu$l of the sample, 600 $\mu$l of the 1st reagent was added, and this was left to stand at 37° C. for 10 minutes, and then 160 $\mu$l of the 2nd reagent was added thereto, and this was left to stand at 37° C. for 5 minutes. Further, 20 $\mu$l of the 3rd reagent was added thereto, and this was left to stand at room temperature for 5 minutes, and then the absorbance of the reaction solution was measured with a wavelength of 550 nm. The results are shown in FIG. 4.

Figure 4:
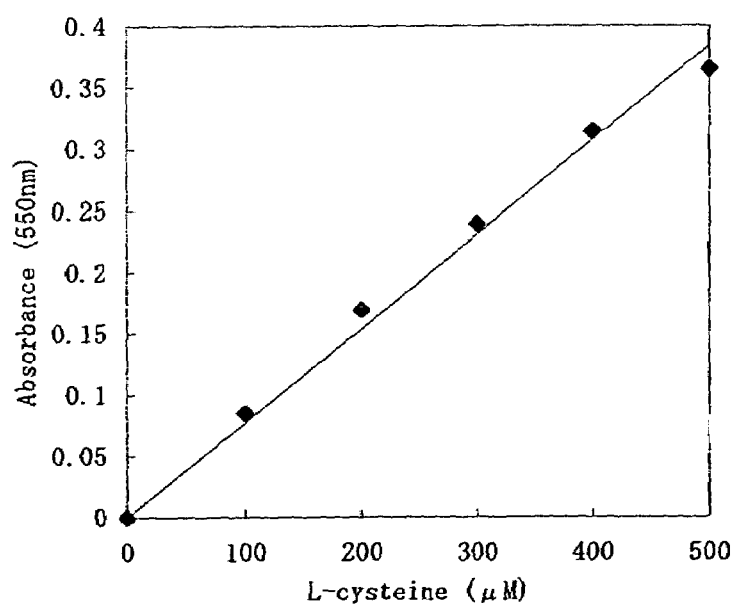
FIG. 4 is a graph showing the results of quantitative determination of cysteine by a color development-accelerating method.

From the results of FIG. 4, increase in the absorbance was confirmed corresponding to the concentration of the cysteine, and it was found that this correlation was quantitative. From the results, it was also found that cysteine can be measured by utilizing the acceleration reaction for the formation of complexes between the metal ions and metal indicator.

INDUSTRIAL APPLICABILITY

As described above, according to the present invention, it is possible to quantitatively determine hydrogen sulfide or sulfide ions in a sample conveniently with high sensitivity. Further, it is also possible to quantitatively determine a specific substance in a sample conveniently with high sensitivity, by adding to a sample containing a specific substance, a component which acts on the specific substance so that the specific substance forms hydrogen sulfide or sulfide ions, and measuring the hydrogen sulfide or sulfide ions by the above quantitative determination method. Accordingly, the present invention can be utilized for, for example, a quantitative determination method of homocysteine, cysteine, etc. in a sample of a living body.

What is claimed is:

1. A method for quantitatively determining hydrogen sulfide or sulfide ions which comprises (a) adding to a sample containing hydrogen sulfide or sulfide ions, (i) metal ions or a compound which liberates said metal ions and (ii) a metal indicator which reacts with the metal ions and resultantly undergoes a color development, the color development being accelerated or inhibited by the hydrogen sulfide or sulfide ions, wherein complexes are formed by the reaction of the metal ions and the metal indicator, and (b) measuring the degree of color development of the metal indicator by determining the amount of the formed complexes and subtracting from said amount the amount of formed complexes when the metal ions are reacted with the metal indicator when no hydrogen sulfide or sulfide ions are present, whereby a decreased amount of the formed complexes indicates an inhibition of color development and corresponds to the amount of the hydrogen sulfide or sulfide ions present in the sample, or an increased amount of formed complexes indicates an acceleration of color development and corresponds to the amount of the hydrogen sulfide or sulfide ions present in the sample.

2. The method according to claim 1, wherein the color development is inhibited and the metal ions are zinc ions or the color development is accelerated and the metal ions are iron ions.

3. The method according to claim 1, wherein the metal indicator is a pyridylazo compound or a nitrosoaminophenol compound.

4. A method for quantitatively determining a specific substance which comprises (a) adding to a sample containing a specific substance, (i) a component which acts on the specific substance so that the specific substance forms hydrogen sulfide or sulfide ions, (ii) metal ions or a compound which liberates said metal ions, and (iii) a metal indicator which reacts with the metal ions and resultantly undergoes a color development, the color development being accelerated or inhibited by the hydrogen sulfide or sulfide ions, wherein complexes are formed by the reaction of the metal ions and the metal indicator, and (b) measuring the degree of color development of the metal indicator by determining the amount of the formed complexes and subtracting from said amount the amount of formed complexes when the metal ions are reacted with the metal indicator when no hydrogen sulfide or sulfide ions are present, whereby a decreased amount of the formed complexes indicates an inhibition of color development and corresponds to the amount of the hydrogen sulfide or sulfide ions present in the sample, or an increased amount of the formed complexes indicates an acceleration of color development and corresponds to the amount of the hydrogen sulfide or sulfide ions present in the sample.

5. The method according to claim 4, wherein the color development is inhibited and the metal ions are zinc ions or the color development is accelerated and the metal ions are iron ions.

6. The method of claim 4, wherein the metal indicator is a pyridylazo compound or a nitrosoaminophenol compound.

7. The method of claim 4, wherein the specific substance is homocysteine, and the component which acts on the specific substance so that the specific substance forms hydrogen sulfide or sulfide ions, is an enzyme (E1) which acts on the homocysteine so that the homocysteine forms hydrogen sulfide.

8. The method according to claim 7, wherein the enzyme (E1) is a substance which catalyzes a substitution reaction to the homocysteine in the presence of a thiol compound.

9. The method according to claim 8, wherein the enzyme (E1) is O-acetylhomoserine-lyase.

10. The method according to claim 8, wherein the thiol compound is at least one compound selected from the group consisting of methane thiol, 2-mercaptoethanol, dithiothreitol, thioglycerol and cysteamine.

11. The method according to claim 4, wherein the specific substance is cysteine, and the component which acts on the specific substance so that the specific substance forms hydrogen sulfide or sulfide ions, is an enzyme (E2) which acts on the cysteine so that the cysteine forms hydrogen sulfide.

12. The method according to claim 11, wherein the enzyme (E2) is a substance which catalyzes a substitution reaction to the cysteine in the presence of a thiol compound.

13. The method according to claim 12, wherein the enzyme (E2) is O-acetylserine-lyase.

14. The method according to claim 12, wherein the thiol compound is at least one compound selected from the group consisting of methane thiol, 2-mercaptoethanol, dithiothreitol, thioglycerol and cysteamine.

15. The method according to claim 1, wherein the metal indicator is a pyridylazo compound that is selected from the group consisting of 2-(5-bromo-2-pyridylazo)-5-(N-n-propyl-N-(3-sulfopropyl)amino]phenol sodium salt and 2-(5-nitro-2-pyridylazo)-5-(N-n-propyl-N-(3-sulfopropyl) amino]phenol sodium salt.

16. The method according to claim 1, wherein the metal indicator is a nitrosoaminophenol compound that is selected from the group consisting of 2-nitroso-5-[N-n-propyl-N-(3-sulfopropyl)amino]phenol and 2-nitroso-5-[N-ethyl-N-(3-sulfopropyl)amino]phenol.

17. The method according to claim 1, wherein the color development is inhibited and the metal ions are zinc ions; and the metal indicator is a pyridylazo compound.

18. The method according to claim 1, wherein the color development is accelerated and the metal ions are iron ions; and the metal indicator is a pyridylazo compound.

19. The method according to claim 1, wherein the color development is accelerated and the metal ions are iron ions; and the metal indicator is a nitrosoaminophenol compound.

20. The method according to claim 1, wherein the color development is accelerated and the metal ions are iron (II) ions or iron (III) ions.

* * * * *